(12) United States Patent
Horn et al.

(10) Patent No.: US 9,675,414 B2
(45) Date of Patent: Jun. 13, 2017

(54) RENAL NERVE MODULATION BALLOON AND METHODS OF MAKING AND USING THE SAME

(71) Applicant: Boston Scientific Scimed, Inc., Maple Grove, MN (US)

(72) Inventors: Daniel J. Horn, Shoreview, MN (US); Robert N. Squire, Maple Grove, MN (US); Adam Joseph Royer, Brooklyn Park, MN (US); Jeffrey S. Lindquist, Maple Grove, MN (US); John J. Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 413 days.

(21) Appl. No.: 14/012,573

(22) Filed: Aug. 28, 2013

(65) Prior Publication Data

US 2014/0074083 A1   Mar. 13, 2014

Related U.S. Application Data

(60) Provisional application No. 61/700,461, filed on Sep. 13, 2012.

(51) Int. Cl.
*A61B 18/14* (2006.01)
*A61B 18/18* (2006.01)
*A61B 18/00* (2006.01)

(52) U.S. Cl.
CPC .......... *A61B 18/18* (2013.01); *A61B 18/1492* (2013.01); *A61B 2018/00011* (2013.01); *A61B 2018/0022* (2013.01); *A61B 2018/00434* (2013.01); *A61B 2018/00577* (2013.01); *A61B 2018/00821* (2013.01); *F04C 2270/041* (2013.01); *Y10T 156/10* (2015.01)

(58) Field of Classification Search
CPC ........ A61B 18/1492; A61B 2018/0022; A61B 2018/00511; A61B 2018/00434; A61B 2018/00821; A61B 2018/00255
USPC .......................................................... 606/41
See application file for complete search history.

(56) References Cited

U.S. PATENT DOCUMENTS

| | | | |
|---|---|---|---|
| 5,290,306 A | 3/1994 | Trotta et al. | |
| 5,512,051 A | 4/1996 | Wang et al. | |
| 5,613,979 A | 3/1997 | Trotta et al. | |
| 5,876,374 A | 3/1999 | Alba et al. | |
| 6,464,697 B1 * | 10/2002 | Edwards | A61B 18/12 606/41 |
| 6,605,056 B2 | 8/2003 | Eidenschink et al. | |
| 6,752,805 B2 * | 6/2004 | Maguire | A61B 18/1492 606/32 |

(Continued)

FOREIGN PATENT DOCUMENTS

| | | |
|---|---|---|
| WO | 9935986 | 7/1999 |
| WO | 0066021 | 11/2000 |

(Continued)

*Primary Examiner* — Thomas Giuliani

(57) ABSTRACT

An expandable medical balloon for transmitting radiofrequency energy, the medical balloon comprising at least one polymeric electrically-insulating layer and at least one polymeric electrically-conductive layer, wherein at least portions of the polymeric electrically-insulating layer are moveable relative to the polymeric electrically-conductive in said at least one pressurizable expanded state.

13 Claims, 4 Drawing Sheets

(56) References Cited

U.S. PATENT DOCUMENTS

| | | |
|---|---|---|
| 7,314,480 B2 | 1/2008 | Eidenschink et al. |
| 7,686,841 B2 | 3/2010 | Eidenschink et al. |
| 7,736,362 B2 | 6/2010 | Eberl et al. |
| 8,043,673 B2 | 10/2011 | Lee et al. |
| 8,168,275 B2 | 5/2012 | Lee et al. |
| 8,551,096 B2 * | 10/2013 | Perry et al. ............ 606/76 |
| 2005/0171525 A1 * | 8/2005 | Rioux ............ A61B 18/14 606/41 |
| 2005/0273149 A1 | 12/2005 | Tran et al. |
| 2007/0129720 A1 | 6/2007 | Demarais et al. |

FOREIGN PATENT DOCUMENTS

| | | |
|---|---|---|
| WO | 0195820 | 12/2001 |
| WO | 2005041810 | 5/2005 |
| WO | 2010132703 | 11/2010 |

\* cited by examiner

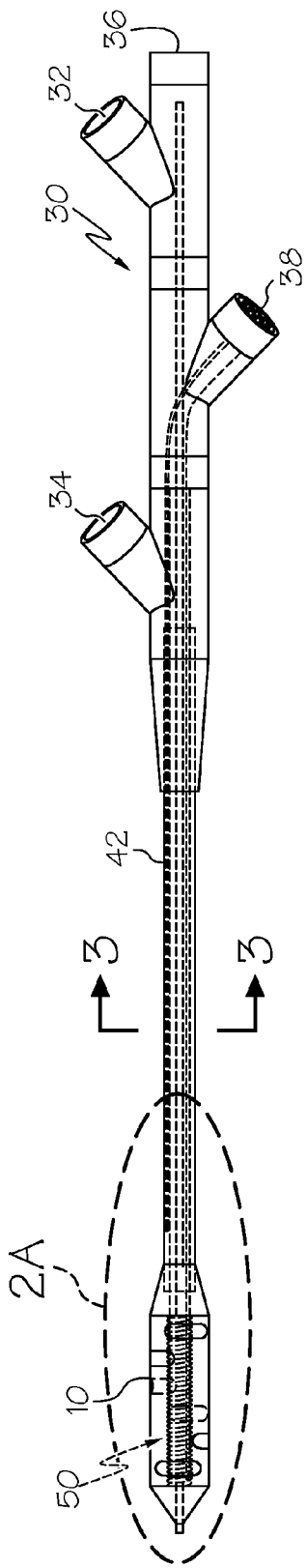
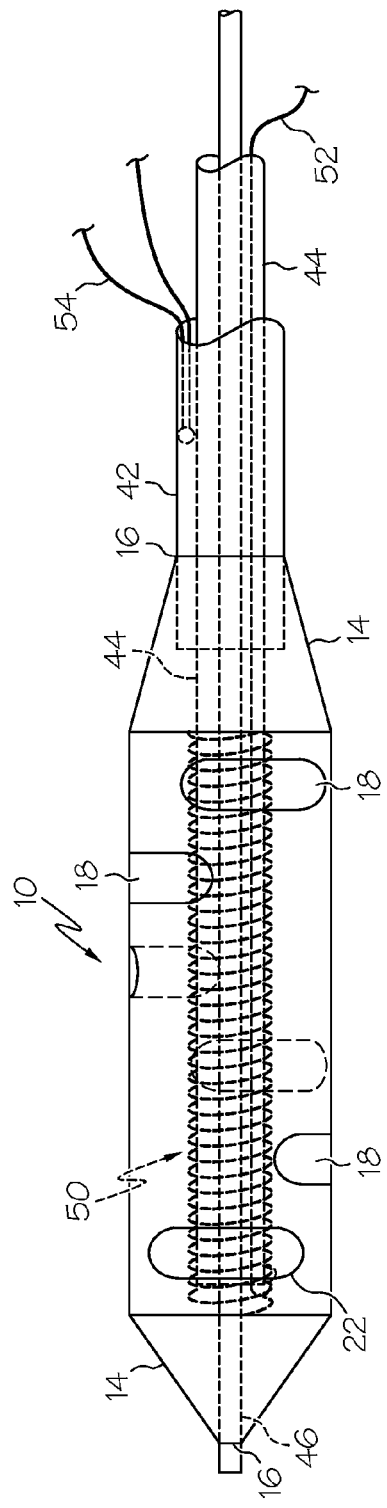

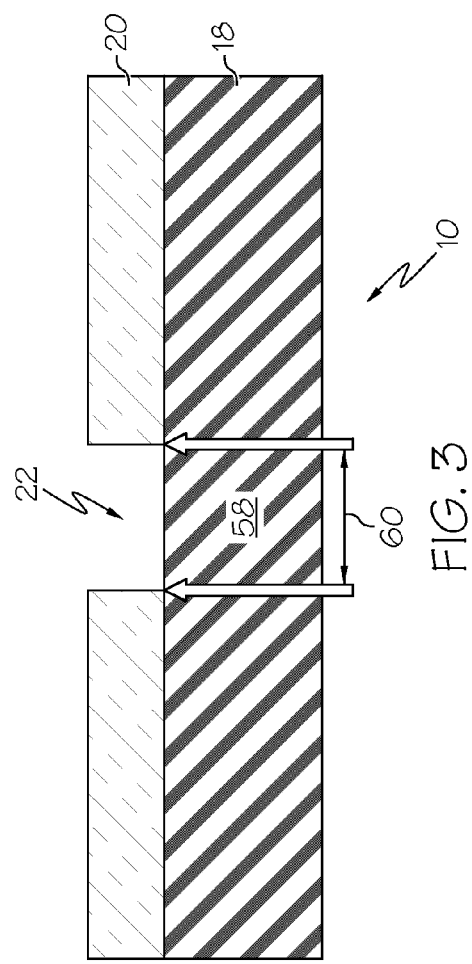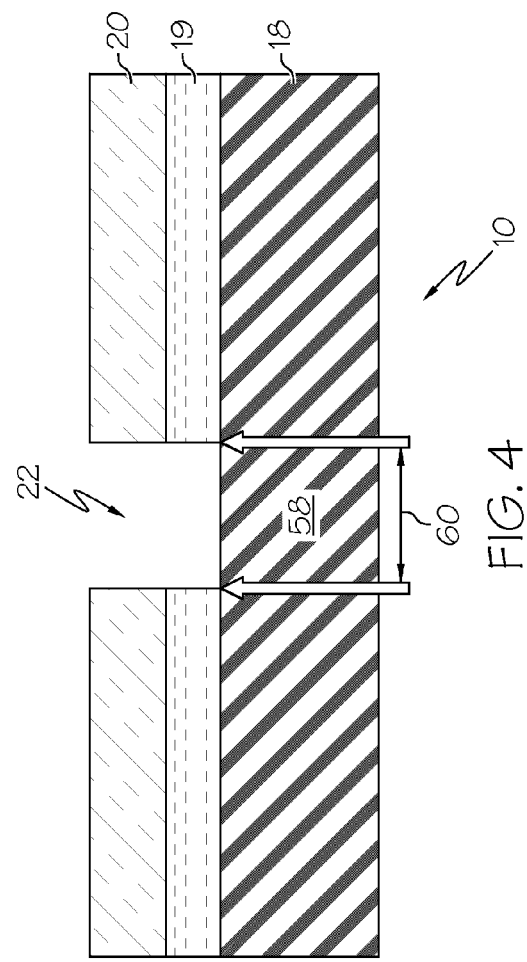

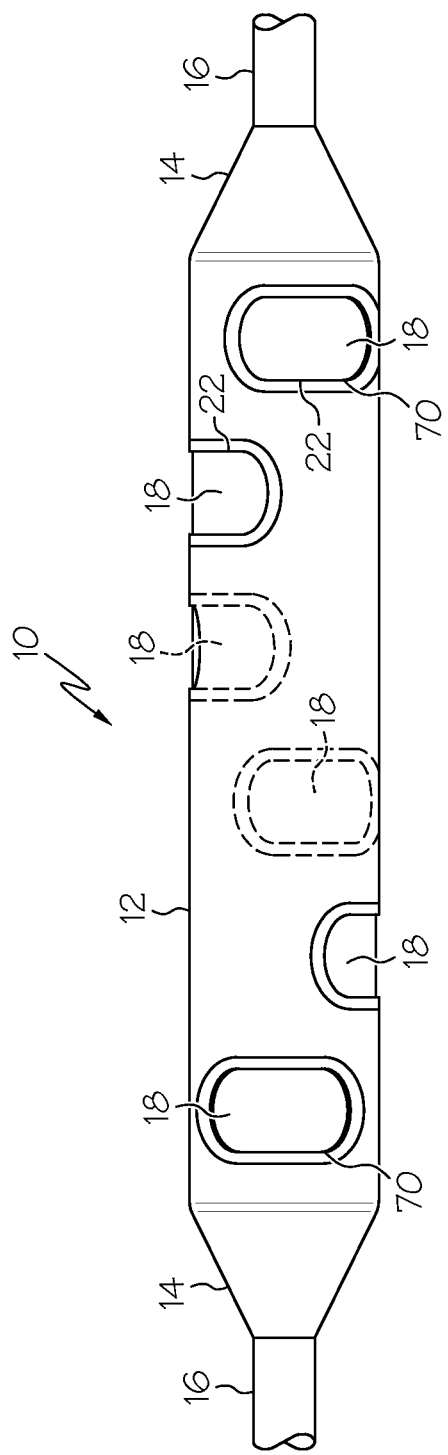

RENAL NERVE MODULATION BALLOON AND METHODS OF MAKING AND USING THE SAME

CROSS-REFERENCE TO RELATED APPLICATIONS

This application claims priority to U.S. Patent Provisional Application No. 61/700,461, filed Sep. 13, 2012, the entire contents of which are hereby incorporated herein by reference.

BACKGROUND OF THE INVENTION

The present invention is directed to devices for percutaneous renal artery denervation, particularly expandable balloons constructed of energy-conductive polymers and to methods of making and using the same.

Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal artery denervation can reduce blood pressure, and may be a viable treatment option for many patients with hypertension who do not respond to conventional drugs.

Ultrasound, radiofrequency energy, microwave energy, direct heating elements, and balloons with heat or energy sources may be applied to a region of sympathetic nerves.

A specific method for treatment of the renal sympathetic nerves involves a percutaneous, catheter-based therapy that uses radiofrequency energy to disrupt the renal sympathetic nerves. This method involves the use of an expandable polymeric balloon having an electrically-insulating layer and an electrically-conductive layer. The balloon is advanced to the treatment site, expanded with an electrically-conductive inflation fluid, and radiofrequency energy is transmitted through the balloon via the use of, for example, an electrically-conductive metallic band disposed within the balloon. Energy is then transmitted through windows that make up the electrically-conductive layer of the balloon.

Pinhole formation has been found to be one issue that can occur during expansion and transmission of radiofrequency energy through the balloon, typically at the interface of the windows when a temperature and resultant modulus differential develops between the inner electrically-conductive low impedance layer and the electrically-insulating, high impedance layer.

There remains a need in the art for an improved renal denervation balloon that is resistant to pinhole formation, and is robust to high current densities.

SUMMARY OF THE INVENTION

These and other aspects, embodiments and advantages of the present disclosure will become immediately apparent to those of ordinary skill in the art upon review of the Detailed Description and Claims to follow.

In one aspect, the present invention relates to an expandable medical balloon for transmitting radiofrequency energy, the medical balloon comprising at least one polymeric electrically-insulating layer and at least one polymeric electrically-conductive layer, wherein at least portions of the polymeric electrically-insulating layer are moveable relative to the polymeric electrically-conductive layer in said at least one pressurizable expanded state.

In another aspect, the present invention relates to a method of making an expandable medical balloon for use in radiofrequency treatment including providing a balloon, the balloon comprising a base polymer layer, disposing an intermediate layer on said balloon, said intermediate layer comprising a fugitive material or a lubricant and applying an outer polymer layer to said fugitive layer, wherein one of the base polymer layer and the outer layer is an electrically-conductive layer and one of the base polymer layer and the outer layer is an electrically-insulating layer.

BRIEF DESCRIPTION OF THE DRAWINGS

FIG. 2 is a side view of a catheter assembly with parts shown in phantom.

FIG. 2A is an enlarged view taken at section 2A in FIG. 2 illustrating a balloon disposed about a catheter assembly according to the invention.

FIG. 3 is a partial cross-sectional view of a balloon according to the invention illustrating stress/strain regions at the interface of the windows and the electrically-insulating layer.

FIG. 4 is a partial cross-sectional view of a balloon according to the invention having an intermediate fugitive layer or intermediate lubricious layer.

FIG. 5 is a side view of a balloon according to the invention having an electrically-conductive layer and an electrically-insulating layer with conductive windows.

DETAILED DESCRIPTION OF THE INVENTION

While embodiments of the present disclosure may take many forms, there are described in detail herein specific embodiments of the present disclosure. This description is an exemplification of the principles of the present disclosure and is not intended to limit the disclosure to the particular embodiments illustrated.

Figure 1:
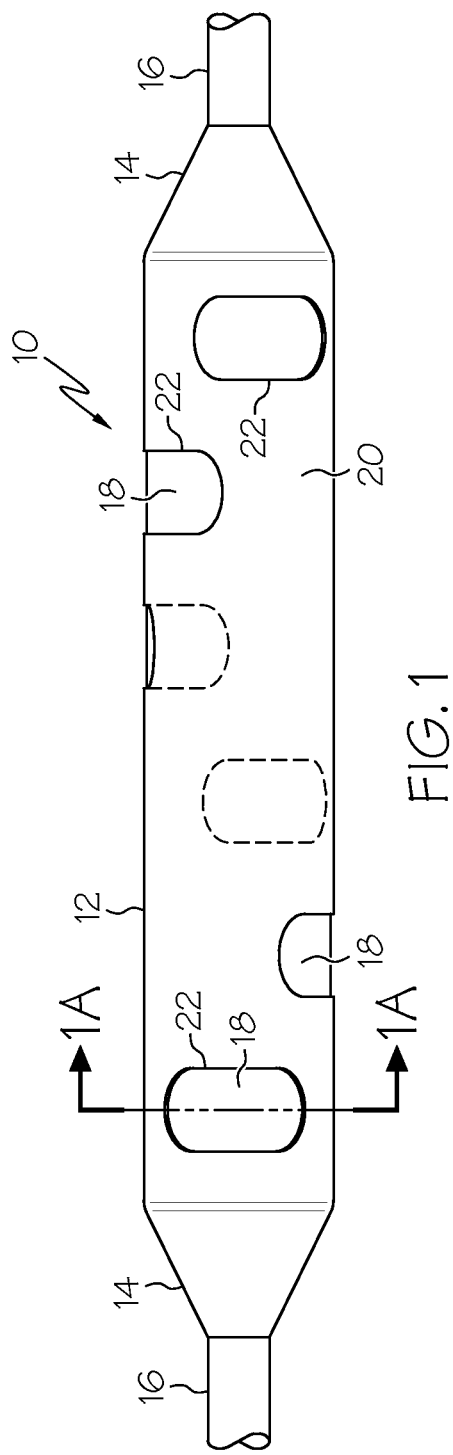
FIG. 1 is a sideview of an embodiment of a balloon according to the invention.

The present invention relates to a renal artery denervation balloon comprising at least one electrically-conductive layer and at least one electrically-insulating layer. Turning now to the figures, FIG. 1 illustrates generally at 10 having a body portion 12, cone portions 14 and waist portions 16. Balloon 10 is formed of two layers including a base layer 18 formed of an electrically-conductive polymer material and an outer layer 20 formed of a non-conductive electrically-insulating polymer material. Windows 22 are formed in the outer layer 20 wherein base layer 18 is exposed.

Windows 22 in this embodiment are shown as having an oval shape. Six windows are shown in this embodiment and are staggered on the balloon in a spiral shape. However, the size and shape of the window as well as the pattern of placement on the balloon may be varied.

Figure 1A:
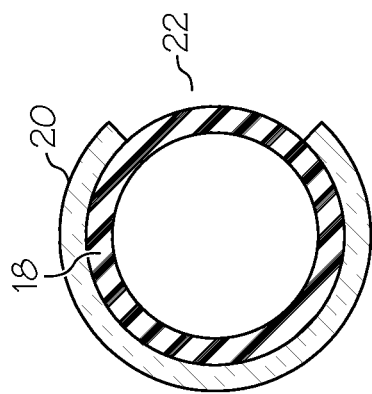
FIG. 1A is a cross-sectional view of the balloon taken at section 1A in FIG. 1.

FIG. 1A is a cross-sectional view of balloon 10 taken at section 1A in FIG. 1.

In other embodiments, the base layer may be formed from the non-conductive electrically-insulating polymer material and the outer layer may be formed from the hydratable electrically-conductive polymer material.

Balloon 20 can be formed from any suitable polymeric material that allows conductivity through the balloon wall.

In some embodiments, the balloon is formed from a hydratable polymer material. Examples of hydratable polymer materials include, but are not limited to, poly(ether-block-amide materials such as PEBAX® MV1074 and MH1657 commercially available from Arkema headquartered in King of Prussia, Pa., polyurethanes such as those available from the Lubrizol Corporation in Wickliffe, Ohio under the tradename of TECOPHILIC® TPUs, for example TECOPHILIC® HP-60D-60 and mixtures thereof.

Suitably, the polymers have a molecular weight of about 10,000 grams/mole to about 50,000 grams/mole, and are extrudable into tubes.

In some embodiments, the hydratable polymer is blended with a non-hydratable polymer, for example, a non-hydratable poly(ether-block-amide) commercially available from Arkema under the tradename of PEBAX® such as PEBAX® 7033 and 7233, non-hydratable polyurethanes, and styrenic block copolymers such as styrene-isoprene-styrene.

The electrically-insulating layer can be formed from any suitable non-conductive polymer material. Examples include, but are not limited to, homopolymeric and copolymeric polyurethanes such as those available from NeoResins, Inc. in Wilmington, Mass. under the tradename of NeoRez such as NeoRez R-967 and from Lubrizol Corp. in Wickliffe, Ohio under the tradename of TECOFLEX® such as TECOFLEX SG-60D and TECOFLEX® SG-85A and These lists of polymer materials are intended for illustrative purposes only, and not as a limitation on the scope of the present invention. Substitution of other hydratable and non-hydratable polymer materials is within the purview of those of ordinary skill in the art.

Balloons of this type are disclosed in commonly assigned U.S. Pat. No. 7,736,362, the entire content of which is incorporated by reference herein.

Balloon 10 can be disposed about the distal end of a catheter assembly 50 as shown in FIGS. 2 and 2A. Catheter 50 includes a manifold 30 which in this embodiment has an inflow port 32 and outflow port 34, a guidewire port 36 and a thermocouple and power jack port 38.

Balloon 10 is disposed on outer catheter shaft 42. Proximal waist portion 16 is secured to the outer shaft 42 and distal waist portion 16 of balloon 10 is secured to the inner shaft 46 of the catheter assembly. Disposed within balloon 10 is an electrically-conductive metallic band 50 which is further fixedly connected to a power wire 52 which is disposed within lumen 45 of an intermediate shaft 44. Metallic band 50 can be formed from any suitable conductive metal such as silver, gold or silver coated copper.

Catheter 50 includes a manifold 30 which in this embodiment has an inflow port 32 and outflow port 34, a guidewire port 36 and a thermocouple and power jack port 38.

The catheter assembly may further include a thermocouple 54 disposed within lumen 43 of outer shaft 42 for accurate temperature measurement.

Balloon 10 can be inflated using an electrically-conductive inflation fluid. Upon activation using radiofrequency (RF) energy, the balloon is activated to provide a low RF energy to the renal artery. The inflation fluid can serve to cool the balloon as well and may be circulated into and out of the balloon during an RF energy treatment cycle.

Normal saline is one example of a suitable inflation fluid.

Balloons are inflated to an internal pressure of about 0.25 atmosphere to about 5 atmospheres, suitably about 0.5 atmosphere to about 3 atmospheres, and more suitably about 0.5 atmosphere to about 2 atmospheres. In some embodiments, the balloon may be inflated to an internal pressure of about 0.25 atmosphere to about 1 atmosphere.

It has been found that when the electrically-insulating polymeric layer and the electrically-conductive polymeric layer are fully adhered to one another, a region of localized stress occurs at the interface of the windows and the insulating layer due to the development of a temperature differential between the electrically-insulating polymer material and the electrically-conductive hydratable polymer material which forms the window as well as the stress created from differential shrinkage of the outer layer and the inner layer. Balloon molding process induced stresses in the window layer are not allowed to relax and become localized upon exposure to high heat. It is surmised that interfacial stress is created from material shrinkage and cooling fluid flow during an RF treatment cycle resulting from heating of the electrically-conductive hydratable polymer material at the window rims. Both resistive heating from the electrical current and conductive heating from body tissue can cause temperature increases at the window sites.

This ultimately can result in balloon pinhole failure at the edge of the windows.

FIG. 3 is a partial view of a balloon 10 having a conductive polymer layer 18 and an electrically-insulating layer 20. During RF energy treatment when the balloon 10 is in an inflated/expanded state, a high temperature zone 58 is created resulting in stressed window edges 60.

It has been found that if the conductive polymer layer 18 and the electrically-insulating layer 20 are movable or slidable relative to one another during use, more of the balloon wall is allowed to strain, thus decreasing the stress at the interface between the layers which occurs in particular, at the interface between the underlying layer and the overlying layer at the balloon window circumference.

It has been found that by dispersing an intermediate fugitive layer or an intermediate lubricious layer between the electrically-conductive layer and the electrically-insulating layer during balloon manufacture provides space between the electrically-conductive layer and the electrically-insulating layer once removed and allows the electrically-conductive layer and the electrically-insulating layer to move or slide relative to one another thus relieving stress in the balloon, particularly at the interface of the balloon windows and the electrically-insulating layer.

In one embodiment, a fugitive intermediate layer is formed by disposing a hydrophilic polymer that is soluble or dissolvable in an aqueous environment between the electrically-conductive layer and the electrically-insulating layer to form a washable intermediate layer.

In this embodiment, a balloon is formed of either the electrically-conductive layer or the electrically-insulating layer by molding. The formed balloon is then sprayed with or dipped in a solution of a hydrogel. The outer layer is then sprayed onto the hydrogel layer. The balloon is soaked in water to remove the fugitive and then dried/vacuumed.

FIG. 4 illustrates an embodiment wherein a hydrophilic water soluble or dissolvable polymer layer or a lubricant layer 19 is dispersed between the electrically-conductive layer 18 and the electrically insulating layer 20 of balloon 10.

Any suitable biocompatible water soluble or dissolvable polymer can be employed herein. Examples of suitable water soluble/dissolvable polymers or oligomers that are washable from between the electrically-conductive layer and the electrically-insulating layer at body temperature include, but are not limited to, low molecular weight poly (vinyl alcohol)s (PVAs), polyethylene oxides (PEOs), poly-acrylamides, poly(meth)acrylic acids, etc.

In another embodiment, a lubricant is disposed between the electrically-conductive layer and the electrically-insulating layer to disrupt adhesion between the electrically-conductive layer and the electrically-insulating layer allowing the layers to move relative to one another and to relieve localized stress/strain in the longitudinal and radial growth directions. Examples of suitable lubricants include, but are not limited to, poly(carboxylic acid)s and silicones. The balloon is formed as described with respect to the hydrogels above.

In yet another alternative embodiment, water is disposed between the electrically-conductive layer and the electrically-insulating layer. A balloon is molded from the electrically-conductive layer. The balloon is then hydrated and the outer layer is disposed thereon. The water can be removed by drying/vacuuming.

EXAMPLES

Example 1

A balloon tube having an inner diameter (ID) of 0.032" and an outer diameter (OD) of 0.070" and a wall thickness of 0.0019" of 100% PEBAX® MV1074 was extruded. The extruded tube was radially expanded in a balloon mold at a temperature of 87 degrees Celsius and pressure of 250 psi. The balloon was heatset in the mold at a temperature of 120° C. for 60 seconds and a pressure of 250 psi. The balloon was removed from the mold and annealed unpressurized at 100° C. for 2 hours to remove any mold induced stresses. It has been found that heatsetting and annealing provides a 25-30% higher passing power over balloons that are not heatset/annealed. The balloon was sprayed with a hydrogel coating, masked with oval shaped masking pieces and sprayed with TECOFLEX® SG-85A TPU and the balloon is dried at 45° C. The masks were removed to reveal the electrically-conductive windows of the base polymer layer. The hydrogel fugitive was washed off the balloon with water and the balloon was dried leaving the electrically-conductive layer and the electrically-insulating layer non-adhered. The resultant 6 mm balloon had a 2× wall thickness as measured by pinching the balloon walls together and measuring with a drop gage of 0.0022" and the electrically-insulating coating had a thickness between about 0.0008" and 0.0016" for a 1× wall. The total area of the windows combined was 0.536 cm$^2$ at 15 psi.

The electrically-conductive layer and the electrically-insulating layer of the balloons formed as described above can be selectively adhered on only portions of the balloon so that the electrically-conductive layer and the electrically-insulating layer are moveable relative to one another on only selective portions of the balloon.

The layers can be selectively adhered using any technique known in the art.

In one embodiment, the balloons are plasma treated to as to provide selective adhesion on only portions of the balloon.

Balloons formed as described above were plasma treated at specific predetermined locations to obtain selective adhesion of the electrically-conductive layer to the electrically-insulating layer. The balloon is inflated to 7 psi and sealed before subjecting to the plasma treatment. The conditions employed for plasma treatment are shown in Table 1 below:

TABLE 1

| Setting | Recipe 8 | Recipe 9 | Recipe 10 |
| --- | --- | --- | --- |
| Gas | Helium (Gas 4) | Oxygen (Gas 2) | Argon (Gas 1) |
| Power (W) | 600 | 600 | 400 |
| Gas flow (SCCM) | 350 | 600 | 150 |
| Time (s) | 360 | 60 | 60 |
| Plate | Ground | Powered | Powered |
| Plate spacing (count from top) | Top plate: slot 2 Bottom plate: 11 | Top plate: slot 2 Bottom plate: 11 | Top plate: slot 2 Bottom plate: 11 |
| Base Pressure (mT) | 100 | 100 | 100 |

Oxygen plasma treatment provided the best adhesion results.

In one embodiment, the electrically-conductive layer and the electrically-insulating layer are selectively adhered so as to leave the layers moveable with respect to one another around at least a portion of the circumference of each of the conductive windows as shown in FIG. 5. Balloon 10 has a body portion 12, cone portions 14 and waist portions 16. Balloon 10 is formed of a polymeric electrically-conductive layer 18 and a polymeric electrically-insulating layer 20. Balloon 10 has windows 22 which comprise the electrically-conductive layer. Around the circumference of each window 22 is an area 70 wherein the electrically-conductive layer and the electrically-insulating layer are not adhered and are moveable with respect to one another.

The present invention provides advantages over previous balloon designs. Balloon designs having the electrically-conductive layer fully adhered to the electrically-insulating layer have been found to fail in pinhole mode during RF treatment cycles at lower current density than desirable. The electrically-conductive window material is under stress from shrinking when exposed to additional heat after the balloon is molded due to differences in the modulus of elasticity of the electrically-conductive layer and the electrically-insulating layer. Additional heat sources include elevated temperatures from sterilization, heat created during RF treatment cycles when current is passed through the electrically-conductive windows of the balloon as well as return heat from the treated body tissue. When the electrically-conductive windows are heated, shrinkage of the material results, causing localized stress at the edge of the window with the end result being pinhole formation near the edge of the window.

Successful RF treatment to kill nerves requires a high enough power per unit window area to get the required ablation depth. Lower power results in lower burn depth and lower treatment efficacy. Non-adhered layers have been found to increase balloon robustness and allow higher power during treatment before pinhole formation occurs.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All published documents, including all US patent documents and US patent publications, mentioned anywhere in this application are hereby expressly incorporated herein by reference in their entirety. Any copending patent applications, mentioned anywhere in this application are also hereby expressly incorporated herein by reference in their entirety. Citation or discussion of a reference herein shall not be construed as an admission that such is prior art.

The invention claimed is:

1. An expandable medical balloon for transmitting radiofrequency energy, the medical balloon comprising at least one pressurizable expanded state and comprising: at least one polymeric electrically-insulating layer; and at least one polymeric electrically-conductive layer comprising an electrically-conductive polymer material selectively adhered to the at least one polymeric electrically-insulating layer; wherein at least portions of an underlying surface of the polymeric electrically-insulating layer are not adhered to and moveable relative to the polymeric electrically-conductive layer in said at least one pressurizable expanded state.

2. The expandable medical balloon of claim 1 wherein the at least one polymeric electrically-conductive layer comprises a hydrophilic electrically-conductive polymer.

3. The expandable medical balloon of claim 2 wherein said hydrophilic electrically-conductive polymer comprises at least one member selected from the group consisting of poly(ether-block-amide)s, polyurethanes and mixtures thereof.

4. The expandable medical balloon of claim 1 wherein said polymeric electrically-insulating layer is entirely disposed over said polymeric electrically-conductive layer.

5. The expandable medical balloon of claim 4 wherein said polymeric electrically-conductive layer comprises windows that are electrically conductive.

6. The expandable medical balloon of claim 5 wherein each of said windows is defined by a circumference and said at least portions of the underlying surface of the polymeric electrically-insulating layer are moveable relative to the polymeric electrically-conductive layer at least around the circumference of each of said windows.

7. The expandable medical balloon of claim 5 wherein said balloon comprises 6 windows.

8. The expandable medical balloon of claim 5 wherein the total area of the windows combined is about 0.1 $cm^2$ to about 0.7 $cm^2$.

9. The expandable medical balloon of claim 1 further comprising a fugitive intermediate layer.

10. The expandable medical balloon of claim 9 wherein said fugitive intermediate layer comprises a hydrophilic polymer.

11. The expandable medical balloon of claim 9 wherein said fugitive intermediate layer comprises a water soluble or water dissolvable polymer.

12. The expandable medical balloon of claim 9 wherein said fugitive intermediate layer comprises a hydrogel.

13. The expandable medical balloon of claim 1 further comprising an intermediate layer, the intermediate layer comprising a lubricant.

* * * * *